United States Patent [19]
Sehgal

[11] Patent Number: 5,997,477
[45] Date of Patent: Dec. 7, 1999

[54] APPARATUS FOR IMAGING AN ELEMENT WITHIN A TISSUE AND METHOD THEREFOR

[75] Inventor: Chandra Sehgal, Wayne, Pa.

[73] Assignee: The Trustees of the University of Pennsylvania, Philadelphia, Pa.

[21] Appl. No.: 08/837,160

[22] Filed: Apr. 14, 1997

[51] Int. Cl.[6] ...................................................... A61B 8/00
[52] U.S. Cl. ............................................................ 600/437
[58] Field of Search ..................................... 600/436, 437, 600/442, 443

[56] References Cited

U.S. PATENT DOCUMENTS

| | | | |
|---|---|---|---|
| 4,338,984 | 7/1982 | Kronberg et al. | 141/331 |
| 4,770,184 | 9/1988 | Greene, Jr. et al. | 128/661.08 |
| 4,771,792 | 9/1988 | Seale | 128/774 |
| 4,819,649 | 4/1989 | Rogers et al. | 128/660.02 |
| 4,867,167 | 9/1989 | Magnin | 128/660.06 |
| 5,038,787 | 8/1991 | Antich et al. | 128/660.01 |
| 5,086,775 | 2/1992 | Parker et al. | 128/660.01 |
| 5,099,848 | 3/1992 | Parker et al. | 128/661.07 |
| 5,273,044 | 12/1993 | Flusberg et al. | 128/659 |
| 5,285,788 | 2/1994 | Arenson et al. | 128/660.05 |
| 5,285,789 | 2/1994 | Chen et al. | 128/662.03 |
| 5,305,752 | 4/1994 | Spivey et al. | 128/661.02 |
| 5,318,028 | 6/1994 | Mitchell et al. | 128/660.08 |
| 5,361,767 | 11/1994 | Yukov | 128/660.06 |
| 5,363,849 | 11/1994 | Suorsa et al. | 128/661.08 |
| 5,370,120 | 12/1994 | Oppelt et al. | 128/660.03 |
| 5,375,470 | 12/1994 | Matsushima et al. | 73/626 |
| 5,402,786 | 4/1995 | Drummond | 128/653.2 |
| 5,515,062 | 5/1996 | Maine et al. | 342/457 |
| 5,685,307 | 11/1997 | Holland et al. | 128/660.01 |

OTHER PUBLICATIONS

Adler, et al., "Quantitative Tissue Motion Analysis of Digitized M–Mode Images: Gestational Differences of Fetal Lung," *Ultrasound in Med. & Biol.*, vol. 16, No. 6, 1990, pp. 561–569.

Dickinson, et al., "Measurement of Soft Tissue Motion Using Correlation Between A–Scans," *Ultrasound in Med. & Biol.*, vol. 8, No. 3, 1982, pp. 263–271.

Bassett, et al., "Breast Sonography," *AJR* 156: 449–455, Mar. 1991.

Eisenesher, et al., "La palpation echographique rythmee Echosismographie," *Journal de Radiologie*, vol. 64, No. 4, 1983, pp. 255–261.

Lefebvre, et al., "A fractal approach to the segmentation of microcalcifications in digital mammograms," *Medical Physics*, vol. 22, No. 4, Apr. 1995, pp. 381–390.

Lerner, et al., "'Sonoelasticity' Images Derived From Ultrasound Signals in Mechanically Vibrated Tissues," *Ultrasound In Med. & Biol.*, vol. 16, No. 3, 1990, pp. 231–239.

Leucht, et al., "Microcalcifications in Sonography," in book entitled *Teaching Atlas of Breast Ultrasound*, 2nd Edition, 1996, pp. 189–204.

Ellen B. Mendelson, "Breast Sonography," in book entitled *Diagnostic Ultrasound* (Rumack, et al.), vol. One Chapter 25, pp. 541–563.

Ophir, et al., "Elastography: A Quantitative Method for Imaging the Elasticity of biological Tissues," *Ultrasonic Imaging*, vol. 13, 1991, pp. 111–134.

Sehgal, et al., "Correlative Study of Properties of Water in Biological Systems Using Ultrasound and Magnetic Resonance," *Magnetic Resonance in Medicine*, vol. 3, 1986, pp. 976–985.

Hans Peter Weskott, "Amplitude Doppler US: Slow Blood Flow Detection Tested with a Flow Phantom[1]," *Radiology*, vol. 202, No. 1, Jan. 1997, pp. 125–130.

Wilson, et al., "Ultrasonic Measurement of Small Displacements and Deformations of Tissue," *Ultrasonic Imaging*, vol. 4, 1982, pp. 71–82.

*Primary Examiner*—Brian L. Casler
*Attorney, Agent, or Firm*—Woodcock Washburn Kurtz Mackiewicz & Norris, L.L.P.

[57] ABSTRACT

Methods and apparatus for detecting microcalcifications in breasts. The methods and apparatus will greatly improve detection of breast microcalcifications and concomitantly increase the early detection of breast cancers. The methods and apparatus described herein activate the resonance frequency of a breast microcalcification, thereby allowing for detection of small masses.

20 Claims, 2 Drawing Sheets

APPARATUS FOR IMAGING AN ELEMENT WITHIN A TISSUE AND METHOD THEREFOR

BACKGROUND OF THE INVENTION

1. Field of the Invention

The invention described herein relates to an apparatus and method for imaging an element within a tissue, for example, imaging a microcalcification within a human breast.

2. Description of the Relevant Art

One of the most common clinical features associated with breast cancer is the presence of microcalcifications. It is often an important sign of early cancer and may be the only abnormality in up to 31% of screening-detected carcinomas. Malignant calcifications often appear in breast as innumerable, irregular salt-like grains. Although the size of calcifications can range from the microscopic up to 2 mm, or more, calcifications typically are between 100 and 500 $\mu$m. Important factors in differential diagnosis include the size, shape, number and spatial distribution of calcium particles. Generally, clusters of at least 5–10 microcalcifications must be observed before malignancy is suspected.

Currently, mammography is the most reliable method for imaging calcifications. Other diagnostic techniques, including sonography, thermography, light scanning, and magnetic resonance imaging, cannot adequately image calcium deposits. Because calcification is an important sign of early breast cancer, it can be a useful marker in ultrasonic screening examinations. Ultrasound is not an ionizing radiation and has no known side effects associated with it, relative to X-ray mammography. This makes it particularly attractive for use on women of all ages on a routine basis. Although state-of-the-art mammography is very sensitive in detecting calcifications, it is low in specificity. The relatively high-false positive mammograms result in a low rate of true positive biopsies, and an attendant significant morbidity and high financial cost. For example, it is estimated that out of nearly half a million biopsies performed annually in the US, about 100,000 are done on the basis of microcalcifications detected by screening mammography. The annual cost of these procedures exceeds $250 to $300 million. Of these biopsies, only 24,000 are likely to be an intraductal carcinoma. That is, only one out of every four biopsies proves to be true-positive. A substantial reduction in cost and morbidity can be achieved if the number of negative breast biopsies is reduced. This can be best accomplished by improving the evaluation of microcalcifications.

Clinical evaluation indicates that current ultrasound systems and methods can be prone to high rates of false-positive and false-negative readings, thereby limiting existing ultrasound imaging to use as an adjunct to X-ray mammography. The current methods of ultrasonic imaging use acoustic reflectivity of the tissues to image breasts. Calcium particles are highly reflective compared to the surrounding soft tissues, yet they are difficult to identify reliably on the sonograms. This is largely due to the high background "noise" in the images caused by the coherent interference of the ultrasonic waves.

There have been many attempts to use ultrasonography to image entities within the body. For example, in U.S. Pat. No. 4,867,167, to Magnin (1989), entitled "Method and Apparatus for Determining and Displaying the Absolute Value of Quantitative Backscatter," a selected point in the body is imaged by detecting and utilizing the backscatter attenuation of an ultrasonic signal. In addition to the backscattered signal from body tissues, Magnin's method also requires the detection and analysis of backscatter attenuation from moving blood at a particular point, which is close to the selected point in the body. However, Magnin does not indicate how backscattered signals may be used to image entities independently of moving blood.

Also, in U.S. Pat. No. 5,038,787 to Antich, et al. (1991), entitled "Method and Apparatus for Analyzing Material Properties Using Reflected Ultrasound," the method and device disclosed identify and use critical angles of reflection to evaluate the mechanical properties of a material, for example bone. However, this device is intended to take measurements locally over a selected area, in order to minimize the effects of any non-homogeneity at the site under investigation. Another disclosed device characterizes, small non-homogeneous masses embedded within soft tissue, thus being inadequate for the detection of microcalcifications in the breast.

In U.S. Pat. No. 4,338,984 to Perez-Mendez, et al. (1982), entitled, "Method and Apparatus for Detecting and/or Imaging Clusters of Small Scattering Centers in the Body," a method and apparatus for imaging clusters of calcification in the breast by ultrasound scattering is disclosed. The apparatus includes a plurality of receiving transducers disposed to receive ultrasound energy scattered by inclusions in the breast. The apparatus also employs a water tank or similar coupling means to couple the transmitted ultrasound signals through to the breast tissue. Furthermore, the apparatus and method rely upon phase differences between among the several received scattered energy signals to locate the scattering clusters. The ultrasound frequency used for cluster detection is adapted to generate scattering signals in a manner dependent upon cluster size. This apparatus and method, however, presume that a cluster is a calcification solely on the basis of particle size. Also, the apparatus can experience speckle interference which can lead to erroneous results. In addition, water tanks are very difficult to use for imaging patients. Generally, in such systems there is significant refraction artifact and the motion of breast loosely suspended in water can be a problem.

The advantages of using ultrasound Doppler techniques are described in U.S. Pat. No. 4,770,184 to Greene, et al. (1988), entitled "Ultrasound Doppler Diagnostic System Using Pattern Recognition." This device employs a frequency-analyzed signal from a pulsed Doppler ultrasound examination that is processed using statistical pattern recognition to assess the presence and extent of arterial disease. Although this system can be used to visualize blood vessel wall calcifications and anatomical variations, it requires the flow of blood through the vessel to produce the Doppler signal. However, Greene, et al. do not suggest a system or method by which non-homogeneous entities embedded within other tissues of the body can be located, characterized, and visualized.

In U.S. Pat. No. 5,318,028 to Mitchell, et al. (1994), entitled "High Resolution Ultrasound Mammography System and Boundary Array Scanner Therefor," an ultrasound mammography system that employs a synthetic array and a boundary array concept is described. Although the synthetic array structure reduces the array hardware complexity and resolves projector depth-of-field problems, it requires the synchronization of transmitted pulses to the time between human heartbeats, so that the body motion induced thereby does not corrupt the scanned image. In this system, the reflection data collected from a scan provides a basis for imaging the breast volume scanned. The nature of the tissue is determined by the shape and relative contrast of the image, as determined from the reflectivity characteristics.

This system is ostensibly limited to applications where the relative movement between the array and objects in the scanned volume is not excessive during the scan period. Furthermore, the image will also exhibit speckle which, in turn, will make the detection of calcification difficult.

In U.S. Pat. No. 4,771,792 to Seale (1988), entitled "Non-Invasive Determination of Mechanical Characteristics in the Body," a non-invasive system and method for inducing relatively low-frequency vibrations in a selected element of the human body and detecting the nature of responses for determining mechanical characteristics of the element are provided. In this system, a broad-band ultrasonic transducer is employed to impart an acoustic wave into the body at multiple frequencies below 20 kHz. By sensing variations in the time-frequency components of the reflected waveform relative to the transmitted multi-frequency signal, the mechanical characteristics of the element can be determined on the basis of the parameters of vibration and of the components of the vibration mode-shape and mechanical vibrational impedance of the element under study. However, Seale's system and method do not provide high resolution imaging of the tissue surrounding the element, or the element itself, to permit additional analysis.

High-resolution breast sonography presents several technical challenges. For example, breast tissue is heterogeneous, resulting in rapid diminution of the beam, owing to reflection and scattering from the many impedance mismatches of tissue surfaces. Also, extensive refraction from curved breast tissue interfaces adds to ultrasonic beam defocusing. Masses located in the superficial breast tissues may be distorted or missed because they are in the near field of the transducer.

Under existing technology, the heterogeneous intensity pattern of the beam in the near field may cause echoes from surrounding tissues to appear within a cyst, suggesting that it is a solid mass. For this reason, breast examination with a hand-held transducer typically requires either the use of a fluid offset, or a transducer with a built-in fluid offset. For the former, a suitable fluid offset would be a degassed water-filled bag placed between the transducer and the breast, or a commercially-produced water tank or offset device.

Masses deep in the breast may also be distorted owing to the diverging beam that degrades lateral resolution. This distortion may take the form of blurring of the margins of masses, filling-in of shadows behind small masses, and failure to resolve smaller masses. Although phased-array probes can provide high-resolution imaging of breast tissue, phased-array probes typically image superficial masses improperly unless a transducer offset device is used to bring the mass into the slice-thickness focus.

In general, although the high-resolution systems are able to successfully differentiate between benign cysts and solid malignant masses, high-resolution systems are hard-pressed to image calcifications in the breast and are unable to differentiate those that are malignant from those that are benign. See, for example, "Breast Sonography", by Bassett et al., AJR 156:449–455, March 1991; "Sonographic Demonstration and Evaluation of Microcalcifications in Sonography" by Leucht, et al. Teaching Atlas of Breast Ultrasound, 2nd Edition, 1996, pp. 189–204; and Breast Sonography, Diagnostic Ultrasound, Vol. 1, Ch. 25, pp. 541–563, for additional discussion regarding the benefits and drawbacks of using current ultrasound technology for breast microcalcification characterization.

What is needed then is a method and apparatus for providing high-resolution, high-specificity imaging and characterization of an element in a surrounding tissue, for example, for detecting, characterizing, and displaying microcalcifications in a human breast.

SUMMARY OF THE INVENTION

The aforementioned long-felt needs are solved by an apparatus for imaging an element within a tissue in accordance with the present invention. Preferably, the apparatus comprises an imaging signal transmitter coupled to the tissue for projecting an imaging signal having an imaging frequency to the element, the element reflecting a portion of the imaging signal. The apparatus further comprises a driving signal transmitter coupled to the tissue for projecting a driving signal having a driving frequency to the element so as to cause the element to resonate at an element resonance frequency, a reflected portion of the driving signal being coupled at about the element resonance frequency to the reflected portion of the imaging signal, so as to create a resonance echo signal. A receiver is coupled to the tissue for receiving the resonance echo signal, and a processor is coupled to the receiver for receiving the resonance echo signal and processing the resonance echo signal to provide perceptible signal representative of the element.

Methods for imaging an element within a tissue also solve the aforementioned long-felt needs. Preferably, the methods comprise the steps of imparting a driving signal into the element, the driving signal having a first preselected frequency range, and the element being urged to move in response to the driving signal, imparting an imaging signal into the element, the imaging signal having a second preselected frequency and being frequency-modulated by the movement of the element, a portion of the frequency-modulated signal being reflected from the element as a resonance echo signal, having a characteristic echo profile, receiving the resonance echo signal, and analyzing the characteristic echo profile to generate a perceptible signal representative of the element.

Methods and apparatus for imaging elements within tissues greatly aid in detecting microcalcifications associated with breast cancer. The methods and apparatus taught and claimed herein provide images which are greatly improved over prior techniques and will aid in early detection of breast cancers. The invention will best be understood by those with skill in the art by reading the following detailed description along with the drawings which are first described briefly below.

DESCRIPTION OF THE EMBODIMENTS

Figure 1:
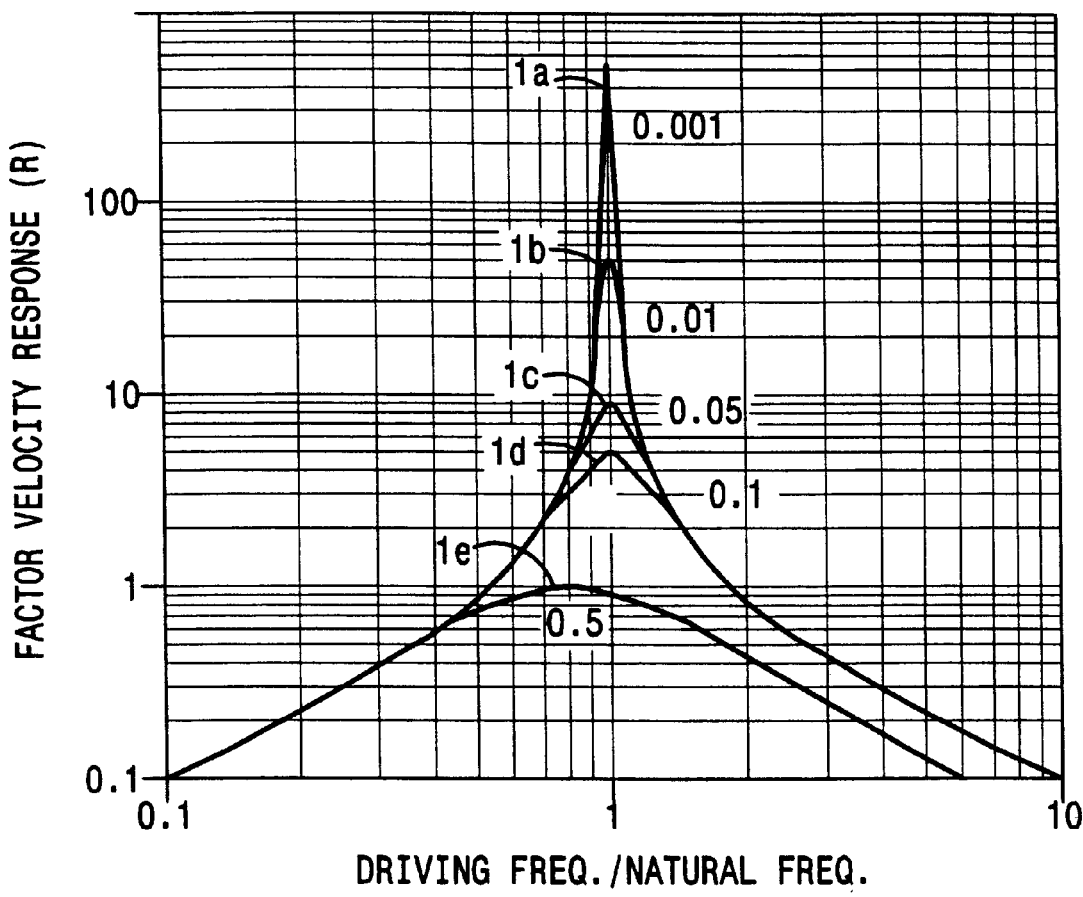
FIG. 1 is a plot of microcalcification velocity responses for plural velocity response factors relative to the ratio of driving frequency to natural frequency.

The invention herein contemplates an apparatus and method for providing high-resolution, high-specificity images of elements in a tissue. Preferred embodiments of the invention include an ultrasonic method and apparatus for detecting and characterizing microcalcifications in a human breast.

Each microcalcification can be made to resonate when activated by a driving signal whose frequency approaches the respective element's resonance frequency. The resonant motion frequency-modulates an imaging signal that is concurrently imparted into, and partially reflected from, the element and the tissue, thus creating a return echo. Accordingly, the invention can be described by the term "Acoustic Resonance Imaging" (ARI). The return echo from the element can have a response characteristic of either the element alone, or the element relative to the surrounding tissue, thus producing an element characterization of high-specificity.

Currently, the diagnosis of breast cancer is primarily based on the size, shape, and the number of calcifications in the breast, and their spatial distribution. ARI can employ driving signals having frequencies that closely match predicted resonant frequencies for calcifications within a particular range of sizes. Element resonance at preselected frequencies can be highly indicative of the presence of a microcalcification and the existence of a breast cancer. Also, the measurements of adhesive forces between the element and the tissue by ARI can be an independent measure which can provide important characterization data when used alone, or in conjunction with other quantitative factors. For example, in the context of a differential diagnosis based upon breast calcifications, ARI adhesive force measurements, when used with the routine morphometric measurements from mammography, could improve the differentiation between malignant and benign, and may help to reduce the incidence of false-negative breast biopsies.

The technique proposed here can overcome the limitations of calcification detection by exciting the calcium particles at frequencies close to their resonance frequency and imaging their motion by integrating the reflected energy in a Doppler signal. The selective excitation of calcium particles results in high-contrast images relative to the surrounding soft tissue. Also, it is possible to determine the adhesion strength, or adhesion tension, between the calcium deposits and the surrounding tissues by the analysis of ARI resonance echo characteristics. Such adhesive forces are likely to be related to the molecular characteristics of the deposits and the mechanism(s) that cause calcium to nucleate at the specific sites of the tissues.

Currently, one of the most reliable methods of imaging microcalcifications is X-ray mammography. One drawback of using X-ray imaging is the ionizing nature of the X-radiation. In contrast, ultrasonography does not involve ionizing radiation and is considered to have less risk, relative to X-ray mammography, for younger women. X-ray mammography also does not provide information on the forces binding the calcification to the surrounding tissue. Unfortunately, clinical experience indicates that ultrasonography can have high false-positive and false-negative rates.

Because ARI can use an integrated Doppler signal, it tends to not have speckle interference, and microcalcifications can appear as high-contrast objects. Because the detection of smaller objects requires higher contrast, ARI can permit the visualization of smaller calcification particles than is feasible by conventional echography.

It is preferred that the signal used for imaging be sensitive to slow motion, as well as independent of the angle between the beam and the direction of motion, θ. Integrated energy under a Doppler spectrum, also referred to as power amplitude Doppler, is particularly preferred for this purpose because it is sensitive to slow motion, as well as relatively independent of the angle θ.

Microcalcifications typically behave as inhomogeneities "suspended" in the matrix of soft tissue. These inhomogeneities are not freely-floating but are bound to the neighboring tissue by weak forces of adhesion characterized by a force constant k. The magnitude of these forces depends on the wettability, i.e., the hydrophilic/hydrophobic character, of the particles. When exited by vibrations of a driving signal, having angular frequency $\omega_d$ and amplitude $P_{d0}$, the calcium particle of radius r and mass m acts as a damped oscillator, and moves in a manner modelled by:

$$m\ddot{x}+c'\dot{x}+kx=4\pi r^2 P_{d0} \sin \omega_d t \qquad (1)$$

where c' is the viscous damping constant. Solving the differential equation for x gives the response curves for the velocity of the particle.

$$\frac{\dot{x}}{\frac{4\pi r^2 P_{d0}}{\sqrt{km}}} = R \cos(\omega t - \theta) \qquad (2)$$

where, R and θ are $$R = \frac{\omega_d}{\omega_n} \sqrt{(1-\omega_d^2/\omega_n^2)^2 + (2\zeta\omega_d/\omega_n)^2} \qquad (3)$$

$$\theta = \tan^{-1}\left(\frac{2\zeta\omega_d/\omega_n}{1-\omega_d^2/\omega_n^2}\right), \qquad (4)$$

respectively. $\omega_n$ is the undamped natural frequency, also called the element resonance frequency, and equal to $\sqrt{k/m}$. The symbol ζ represents the fraction of critical damping. The curves for velocity response factor R are shown in FIG. 1. Curves 1a–e illustrate the velocity responses for R values of about 0.001, 0.01, 0.05, 0.1 and 0.5 respectively.

The strength of interaction at the calcium/soft tissue interface typically depends on the wettability of the particles. The relationship between wettability and adhesion may be discussed in terms of interfacial tension, which is a function of free energy per unit area of the interface. The work of adhesion, $W_{CS}$, between calcium C and the soft tissue S, is defined as the increase in free energy that results when the two are separated. If γ is the surface tension, then $$W_{CS}=\gamma_C+\gamma_S-\gamma_{CS} \qquad (5)$$

For a contact angle of $\theta_{CS}$ between calcium and soft tissue $$\gamma_C=\gamma_{CS}+\gamma_S \cos \theta_{CS} \qquad (6)$$

or, $$W_{CS}=\gamma_S(1+\cos \theta_{CS}) \qquad (7)$$

The quantity $\gamma_S(1+\cos \theta_{CS})$ is termed as adhesion tension and is a measure of k.

For various biological fluids like saliva, aqueous humor, blood $\gamma_S$ values range from 15–60 dynes/cm. Interstitial fluid, which is primarily responsible for the wetting of calcifications, may have a comparable value and the force constant $k_{CS}$ may range between 10–100 dynes/cm depending upon surface morphology, contact angle θ, and $\gamma_S$. Within the bulk of the tissue, the adhesion tension between the neighboring regions is determined by weak physical forces due to the hydrogen bonding. The binding energy of hydrogen bonds typically is on the order of 5–10 Kcal/mole, resulting in the force constant for the tissues, $k_{SS}$, being on the order of $10^5$ dyne/cm.

Figure 2:
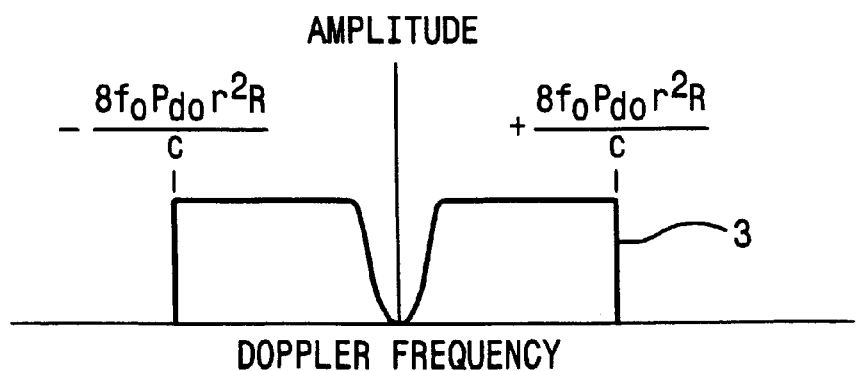
FIG. 2 is a diagram of Doppler signal amplitude relative to Doppler frequency.

FIG. 1 represents velocity responses 1a–e for microcalcification deposits of between about 100 to 500 microns at the driving frequency (abcissca=1) of about 100 Hz. For the surrounding soft tissues, $\omega_d/\omega_n$, is less than $10^{-5}$ and not close to the calcification resonance frequency peak. Thus, the microcalcifications can exhibit strong vibrations in response to the external excitation, whereas the surrounding soft tissue will not. If the medium is insonated with high imaging frequency, $f_0$, simultaneous to external vibrations, the resonance echo signal from the microcalcifications will be frequency-modulated due to Doppler effect. The frequency shift, $\Delta f$, will be, $$\Delta f(t) = \frac{2f_0 F_{d0} R \cos(\omega_d t - \phi)\cos\theta}{c\sqrt{(km)}} \quad (8)$$

where $F_{d0}=4\pi r^2$. At or near resonance, $\omega_d/\omega_n=1$. Therefore, $R=\frac{1}{2}\zeta$, and $\phi=\pi/2$ and the Doppler shift is, $$\Delta f_R(t) = \frac{f_0 F_{d0}\sin(\omega_d t)\cos\theta}{c\zeta\sqrt{km}}$$

where subscript R represents the resonance. The Doppler spectrum will span over the frequencies $$\Delta f_R(t) = \frac{f_0 F_{d0}\sin(\omega_d t)\cos\theta}{c\zeta\sqrt{km}} \quad (9)$$

$$(f+) = \frac{f_0 F_{d0}\cos\theta}{c\zeta\sqrt{km}} \text{ to } (f-) = -\frac{f_0 F_{d0}\cos\theta}{c\zeta\sqrt{km}}$$

as shown in FIG. 2.

If $A_1$ is the amplitude of the signal scattered by resonant structures, the integrated power of the Doppler spectrum, PD, is, $$PD_R = \frac{2f_0\cos\theta}{c}\left(\frac{A^2 F_{d0}}{\zeta\sqrt{km}}\right)_R \quad (10)$$

There are two possibilities for the non-resonant structures: those for which the driving frequency is significantly less than the resonance frequency ($\omega_d \ll \omega_n$), and others that correspond to the condition $\omega_d \gg \omega_n$. The first case is spring (or elasticity) controlled. The soft tissues with individual elements bound by forces like hydrogen bonding and vander waal forces are characterized by this condition. On the other hand, the second case is mass-controlled and describes the behavior of large structures like tendons, and arteries. Following the approach used above the integrated power Doppler for the non-resonant cases can be shown to be, $$PD_{NR}^{\omega_d \ll \omega_n} = \frac{4f_0\cos\theta}{c}\left(\frac{\omega_d A^2 F_{d0}}{k}\right)_{NR}^{\omega_d \ll \omega_n} \quad (11)$$

and $$PD_{NR}^{\omega_d \gg \omega_n} = \frac{4f_0\cos\theta}{c}\left(\frac{A^2 F_{d0}}{\omega_d^m}\right)_{NR}^{\omega_d \gg \omega_n} \quad (12)$$

The integrated power Doppler signal from the resonant microcalcifications relative to the non-resonant background soft tissue is the ratio of Equations 10 and 11, $\beta_{PD}$, $$\beta_{PD} = \frac{1}{2\zeta\omega_d}\left(\frac{A_c}{A_s}\right)^2\left(\frac{r_c}{r_s}\right)^2\left(\frac{k_s}{\sqrt{k_c m_c}}\right) \quad (13)$$

where subscripts C and S represent calcium deposit and soft tissues, respectively. For simplicity if one assumes the backscatter from the various tissue structures to be comparable, and $\zeta=0.5$, then 100 micron calcium particles surrounded by cells of 10 microns will give a power Doppler signal $10^5$–$10^6$ times stronger than that from the neighboring regions. Because log compression is generally used to display images, in principle, calcifications should appear 5–6 times brighter than the surrounding regions.

Figure 3:
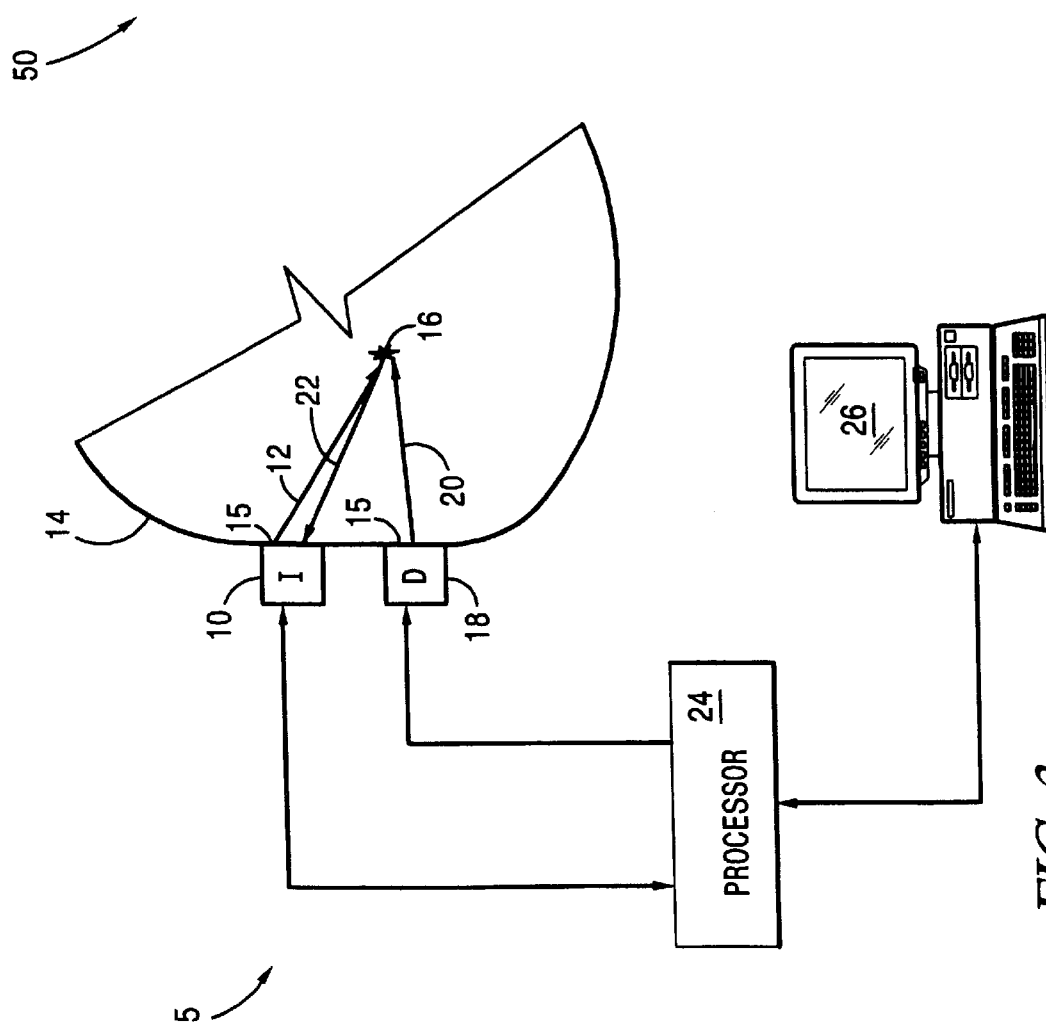
FIG. 3 is a diagram of an embodiment of the apparatus according to the invention.

In one presently preferred embodiment of the invention, illustrated in FIG. 3, apparatus 5 includes transducers 10, 18, processor 24, and image display 26. Transducer 10 includes an imaging transmitter which projects imaging signal 12 to element 16. Transducer 10 is preferred to be coupled to tissue 14 by well-known coupling techniques including, for example, a coupling gel 15. A skilled artisan would recognize that other coupling techniques also may be used, including those that may be physically integrated with transducer 10. It is preferred that the imaging signal transmitter in transducer 10 project imaging signal 12 at a suitable imaging frequency. In the case of a human breast, an imaging frequency of about 6 megahertz is suitable. A portion of imaging signal 12 is reflected from element 16 in a manner proportionate to the inherent reflectivity of element 16. A driving signal transmitter 18 projects a driving signal 20 to element 16. As with transducer 10, transmitter 18 also is preferred to be coupled to tissue 14, for example, by coupling gel 15. Because each element can have an element resonance frequency, driving signal transmitter 18 can provide a driving signal 20 which is user selectable such that the frequency of signal 20 can be made to approximate the element resonance frequency of element 16. Element 16 resonates, responsive to signal 20, and couples a reflected portion of the driving signal to the reflected portion of imaging signal 12 thereby creating a resonance echo 22. Transducer 10 also can serve as a receiver for resonance echo 22. Resonance echo 22 can have a characteristic echo profile, which profile can be representative of element size, element shape, element composition, and element distribution. The characteristic echo profile also can contain information regarding the adhesive force, for example, the adhesion tension, between element 16 and tissue 14. The characteristic echo profile also can include a power Doppler signal therein, which is representative of the element. In light of the above, resonance echo 22 can provide a response characteristic of the element alone, the element relative to the tissue, or both. In order to adequately excite element 16 to resonate, it is preferred that driving signal transmitter 18 provide driving signal 20 at a frequency of between about 20 Hertz and about 2,000 Hertz. In general, it is preferred that the ratio of the driving frequency to the element resonance frequency be between about 0.1 and about 10. Where element 16 is a calcium-based inhomogeneity, and the tissue is the soft tissue of the breast, the size of element 16 can be between about 10 micrometers and about 2 millimeters. Signal transmitter 18 also can provide a multi-frequency driving signal, having signal energy at multiple frequencies to sonographically illuminate the most common range of element sizes that are anticipated. For example, microcalcifications in the human breast typically are between 100 micrometers and 500 micrometers in size.

Figure 4:
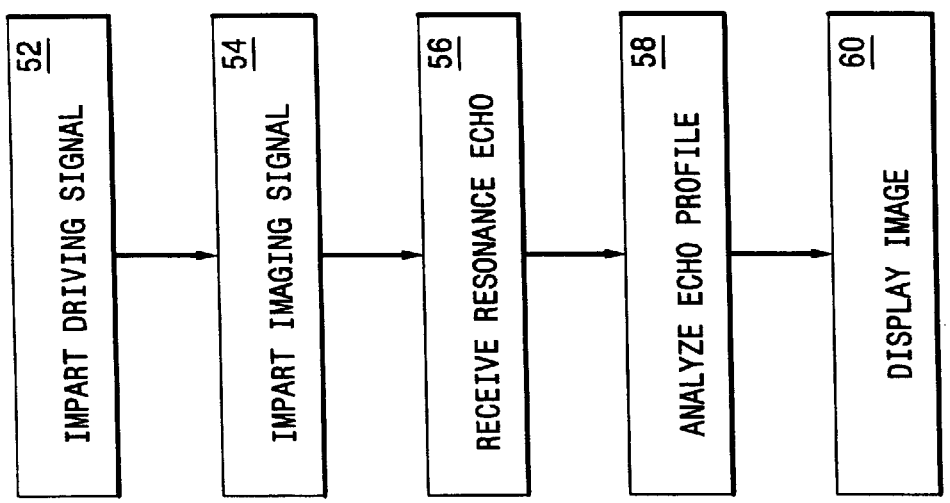
FIG. 4 is a flow diagram of an embodiment of the method according to the invention.

FIG. 4 is a full diagram of the method 50 according to the disclosed invention. The first step of the method includes imparting driving signal 52 into the element, thereby urging the element to move responsive to that driving signal. The driving signal could be first preselected or scanned over a frequency range. For example, for calcifications in the human breast, the driving signal can be between about 20 Hertz and about 2,000 Hertz. Also, the method includes imparting an imaging signal 54 into the element at a second preselected frequency. At least a portion of the imaging signal is frequency-modulated by the movement of the element and a portion of this frequency-modulated signal is reflected from the element as a resonance echo. As with the apparatus in FIG. 1, the resonance echo can have a characteristic echo profile, which can be representative of element size, element shape, element composition, and element distribution. The characteristic profile also can be representative of an adhesive force between the element and the tissue. Some of the imaging signal is reflected from other structures within the tissue e.g. heterogeneous tissues within the breast, which when reflected from the structures generates an imaging echo. Method 50 continues with receiving the resonance echo, step 56, and the imaging echo. Because the resonance echo has a characteristic echo profile, the method can include analyzing the echo profile 58 to generate a perceptive signal representative of the element. Where desired, the method can include displaying the representative perceptible signal, step 60, so that the element can be visualized. In a preferred embodiment of the invention, the step of analyzing the characteristic profile can include the step of performing an integrated Doppler analysis of the profile. The integrated Doppler analysis can, in turn, be used to provide a visual display of the element and the tissue. In the context of breast cancer diagnosis, the method herein can used to detect, characterize, and visualize microcalcifications within the human breast.

All publications mentioned in this specification are indicative of the level of skill of those skilled in the art to which this invention pertains. All publications are herein incorporated by reference to the same extent as if each individual publication was specifically but individually indicated to be incorporated by reference.

While specific embodiments of practicing the invention have been described in detail, it will be appreciated by those skilled in that art that various modifications and alternatives to those details could be developed in light of the overall teachings of the disclosure. Indeed, a skilled artisan would recognize that, although the invention has been described in terms of imaging a microcalcification in a human breast, the apparatus and method illustrated in detail herein also can be used to detect, characterize, and visualize other types of inhomogeneous elements located within other types of tissues or structures. Accordingly, the particular arrangements of the methods and apparatus disclosed are meant to be illustrative only and not limiting to the scope of the invention, which is to be given the full breadth of the following claims, and any and all embodiments thereof.

What is claimed is:

1. An apparatus for imaging an element within a tissue, comprising:
   a. an imaging signal transmitter adapted to be coupled to the tissue for projecting an imaging signal having an imaging frequency to the element, the element reflecting a portion of the imaging signal;
   b. a driving signal transmitter adapted to be coupled to the tissue for projecting a driving signal having a driving frequency to the element so as to cause the element to resonate at an element resonance frequency, a reflected portion of the driving signal being coupled at about the element resonance frequency to the reflected portion of the imaging signal so as to create a resonance echo signal;
   c. a receiver adapted to be coupled to the tissue for receiving at least the resonance echo signal; and
   d. a processor adapted to be coupled to the receiver for receiving the resonance echo signal and processing at least one of the amplitude and the power of the resonance echo signal to provide a perceptible signal representative of the element.

2. The apparatus of claim 1 wherein the processor provides a power Doppler signal representative of the element.

3. The apparatus of claim 1 wherein the resonance echo signal represents a response characteristic of at least one of (a) the element, and (b) the element relative to the tissue.

4. The apparatus of claim 3 wherein the response characteristic is at least one of element size, element shape, element composition, element distribution, and an adhesive force between the element and the tissue.

5. The apparatus of claim 1 wherein the imaging signal has a frequency of 6 megahertz.

6. The apparatus of claim 1 wherein the driving frequency is between 20 Hertz and 2,000 Hertz.

7. The apparatus of claim 1 wherein the ratio of the driving frequency to the element resonance frequency is between 0.1 and 10.

8. The apparatus of claim 1 wherein the driving signal is a multi-frequency driving signal having signal energy at a plurality of frequencies.

9. An apparatus for imaging a calcification within a breast, comprising:
   a. an imaging signal transmitter adapted to be coupled to the breast and the calcification for projecting to the calcification an imaging signal having an imaging frequency, the calcification reflecting a portion of the imaging signal;
   b. a driving signal transmitter adapted to be coupled to the calcification for projecting a driving signal having a driving frequency to the calcification so as to cause the calcification to resonate at a calcification resonance frequency, a reflected portion of the driving signal being frequency-modulated at the calcification resonance frequency onto the reflected portion of the imaging signal so as to create a resonance echo signal;
   c. a resonance echo receiver adapted to be coupled to the calcification for receiving at least the resonance echo signal; and
   d. a resonance echo processor adapted to be coupled to the resonance echo receiver for receiving the resonance echo signal and performing a power Doppler analysis on the resonance echo signal so as to provide a perceptible signal representative of the calcification.

10. The apparatus of claim 9 further comprising an image display coupled to the resonance echo processor for converting the perceptible signal into a visual image of the calcification within the breast.

11. The apparatus of claim 9 wherein the imaging frequency is 6 megahertz, and the driving frequency is between 20 Hertz and 2,000 Hertz.

12. A method for imaging an element with a tissue, comprising the steps of:
   a. imparting a driving signal into the element, the driving signal having a first preselected frequency range, and the element being urged to move responsive to the driving signal;
   b. imparting an imaging signal into the element, the imaging signal having a second preselected frequency and being frequency-modulated by the movement of the element, a portion of the frequency-modulated signal being reflected from the element as a resonance echo signal having a characteristic echo profile;

c. receiving at least the resonance echo signal; and d. analyzing the characteristic echo profile to generate a perceptible signal representative of the element.

13. The method of claim 12, further comprising the step of displaying the representative perceptible signal so that the element can be visualized.

14. The method of claim 12 wherein the step of analyzing the characteristic echo profile includes the step of performing an integrated Doppler analysis of the profile.

15. The method of claim 12 wherein the first preselected frequency range is between 20 Hertz and 2,000 Hertz.

16. The method of claim 12 wherein the second preselected frequency is 6 megahertz.

17. The method of claim 12 wherein the characteristic echo profile is representative of at least one of element size, element shape, element composition, element distribution, and an adhesive force between the element and the tissue.

18. The method of claim 12 wherein step (b) of imparting the imaging signal also includes the step of imparting the imaging signal into the tissue, a second portion of the imaging signal being reflected from the tissue as an imaging echo signal, and further comprising the step of analyzing the imaging echo signal to generate a perceptible signal representative of the tissue.

19. A method for imaging a calcification within a breast, comprising the steps of:

a. imparting a driving signal into the calcification, the driving signal having a frequency of between 20 Hertz and 2,000 Hertz, and the calcification being urged to resonate responsive to the driving signal;

b. imparting an imaging signal into the calcification, the imaging signal having a frequency of about 6 megahertz, the imaging signal being frequency-modulated by the resonation of the calcification so as to form a resonance echo signal having a characteristic echo profile, the characteristic echo profile being characteristic of at least one of calcification size, calcification shape, calcification composition, calcification distribution, and an adhesion tension between the calcification and the breast tissue;

c. receiving the resonance echo signal;

d. analyzing the characteristic echo profile to generate perceptible signals representative of the calcification and the breast tissue, the analyzing including performing an integrated Doppler analysis of the resonance echo signal; and e. displaying the representative perceptible signals so that the calcification can be visualized within the breast.

20. The method of claim 19 wherein the driving signal is a multi-frequency driving signal having signal energy at a plurality of frequencies.

* * * * *

UNITED STATES PATENT AND TRADEMARK OFFICE
CERTIFICATE OF CORRECTION

PATENT NO. : 5,997,477
DATED : December 7, 1999
INVENTOR(S) : Chandra Sehgal It is certified that error appears in the above-identified patent and that said Letters Patent is hereby corrected as shown below:

Col. 2, line 28, after "differences" delete "between"; and
Col. 9, line 32, after "can" insert --be--.

Signed and Sealed this

Fourteenth Day of November, 2000

Attest:

Q. TODD DICKINSON

*Attesting Officer*    *Director of Patents and Trademarks*